(12) United States Patent
Long

(10) Patent No.: US 7,758,579 B2
(45) Date of Patent: Jul. 20, 2010

(54) BIPOLAR PROBE WITH AN INJECTION NEEDLE

(75) Inventor: Gary L. Long, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 635 days.

(21) Appl. No.: 11/434,498

(22) Filed: May 15, 2006

(65) Prior Publication Data

US 2007/0265618 A1 Nov. 15, 2007

(51) Int. Cl.
A61B 18/14 (2006.01)
(52) U.S. Cl. .............................. 606/50; 606/48; 606/49
(58) Field of Classification Search .................. 604/21, 604/22; 606/48–50, 44
See application file for complete search history.

(56) References Cited

U.S. PATENT DOCUMENTS

| | | | |
|---|---|---|---|
| 3,964,477 A | | 6/1976 | Ellis et al. |
| 4,269,174 A | | 5/1981 | Adair |
| 4,576,161 A | * | 3/1986 | Mikkelson .................. 128/843 |
| 5,192,280 A | | 3/1993 | Parins |
| 5,330,471 A | | 7/1994 | Eggers |
| 5,403,311 A | * | 4/1995 | Abele et al. .................... 606/49 |
| 5,484,436 A | | 1/1996 | Eggers et al. |
| 5,674,220 A | | 10/1997 | Fox et al. |
| 5,720,718 A | * | 2/1998 | Rosen et al. .................. 604/22 |
| 5,782,859 A | | 7/1998 | Nicholas et al. |
| 5,849,022 A | | 12/1998 | Sakashita et al. |
| 6,022,334 A | | 2/2000 | Edwards et al. |
| 6,071,281 A | | 6/2000 | Burnside et al. |
| 6,086,586 A | | 7/2000 | Hooven |
| 6,273,887 B1 | | 8/2001 | Yamauchi et al. |
| 6,280,458 B1 | | 8/2001 | Boche et al. |
| 6,379,349 B1 | | 4/2002 | Mueller et al. |
| 6,394,998 B1 | | 5/2002 | Wallace et al. |
| 6,428,538 B1 | | 8/2002 | Blewett et al. |
| 6,447,506 B1 | | 9/2002 | Swanson et al. |
| 6,638,275 B1 | | 10/2003 | McGaffigan et al. |
| 6,669,696 B2 | | 12/2003 | Bacher et al. |
| 6,767,349 B2 | | 7/2004 | Ouchi |
| 6,770,072 B1 | | 8/2004 | Truckai et al. |
| 6,918,906 B2 | | 7/2005 | Long |
| 6,969,389 B2 | | 11/2005 | Kidooka |
| 6,980,854 B2 | | 12/2005 | Bernabei |
| 7,278,992 B2 | | 10/2007 | Cropper et al. |
| 2002/0002385 A1 | | 1/2002 | Boche et al. |
| 2003/0078577 A1 | | 4/2003 | Truckai et al. |
| 2003/0191465 A1 | | 10/2003 | Yahagi et al. |
| 2004/0030335 A1 | | 2/2004 | Zenati et al. |
| 2007/0225610 A1 | * | 9/2007 | Mickley et al. ............. 600/509 |

FOREIGN PATENT DOCUMENTS

EP 0997108 5/2000

* cited by examiner

*Primary Examiner*—Lee S Cohen
*Assistant Examiner*—Jaymi Della
(74) *Attorney, Agent, or Firm*—Victor C. Moreno

(57) ABSTRACT

A surgical system including a bipolar generator having a first electrical connection and a second electrical connection, a needle, the needle being formed from a first electrically conductive material and electrically connected to the first electrical connection, and a conductor coaxially disposed over the needle, the conductor being formed from a second electrically conductive material and electrically connected to the second electrical connection, wherein the needle is electrically isolated from the conductor.

15 Claims, 4 Drawing Sheets

BIPOLAR PROBE WITH AN INJECTION NEEDLE

FIELD OF THE INVENTION

The present application relates to medical devices and methods and, more particularly, to medical devices and methods for treating tissue with electrical energy and/or an injectable agent.

BACKGROUND OF THE INVENTION

Non-variceal upper gastrointestinal ("GI") bleeding typically refers blood loss originating at or proximal to the ligament of Treitz. Peptic ulcers have been identified as being a common cause of non-variceal upper GI bleeding. If left untreated, non-variceal upper GI bleeding may lead to anemia-like symptoms (e.g., fatigue, dizziness and chest pain), hepatic encephalopathy, hepatorenal syndrome, shock and death.

Successful treatment of non-variceal upper GI bleeding typically includes addressing the cause of the bleeding and ultimately haemostasis. For example, peptic ulcers may be associated with an infection of *Helicobacter pylori* and, therefore, may require treatment with antibiotics or the like to eradicate the infection and prevent re-bleeding. Haemostasis may be achieved by invasive surgery or by various less invasive endoscopic techniques, such as laser treatment, multipolar electrocautery, heat probing or injections with epinephrine.

While prior art endoscopic haemostasis techniques have presented some success, the re-bleed rate associated with such techniques remains relatively high. For example, the use of electrocautery to stop upper GI bleed often creates a relatively large treated zone on and around the bleeding site, thereby increasing the risk of re-bleeding.

Accordingly, there is a need for an improved apparatus and method for stopping the bleeding and reducing the re-bleeding associated with non-variceal upper GI bleeding.

SUMMARY OF THE INVENTION

In one aspect, a surgical system includes a bipolar generator having a first electrical connection and a second electrical connection, a needle, the needle being formed from a first electrically conductive material and electrically connected to the first electrical connection, and a conductor coaxially disposed over the needle, the conductor being formed from a second electrically conductive material and electrically connected to the second electrical connection, wherein the needle is electrically isolated from the conductor.

In another aspect, a surgical system includes a source of bipolar electrical energy, the source including a first electrical connection and a second electrical connection, a needle defining an internal passageway therein, the needle being formed from a first electrically conductive material and electrically connected to the first electrical connection, a conductor coaxially disposed over the needle, the conductor being formed from a second electrically conductive material and electrically connected to the second electrical connection, and an injectable agent disposed within the internal passageway, wherein the needle is electrically isolated from the conductor.

In another aspect, a method for treating a target tissue with a bipolar device includes positioning a conductor coaxially around a needle such that the needle is electrically isolated from the conductor, wherein a penetrating tip portion of the needle extends distally beyond the conductor, inserting the penetrating tip portion into the target tissue and electrically connecting the needle and the conductor to a source of bipolar electrical energy such that electrical energy flows through the needle and the conductor.

Other aspects of the disclosed bipolar apparatus and methods will become apparent from the following description, the accompanying drawings and the appended claims.

DETAILED DESCRIPTION OF THE INVENTION

Figure 1:
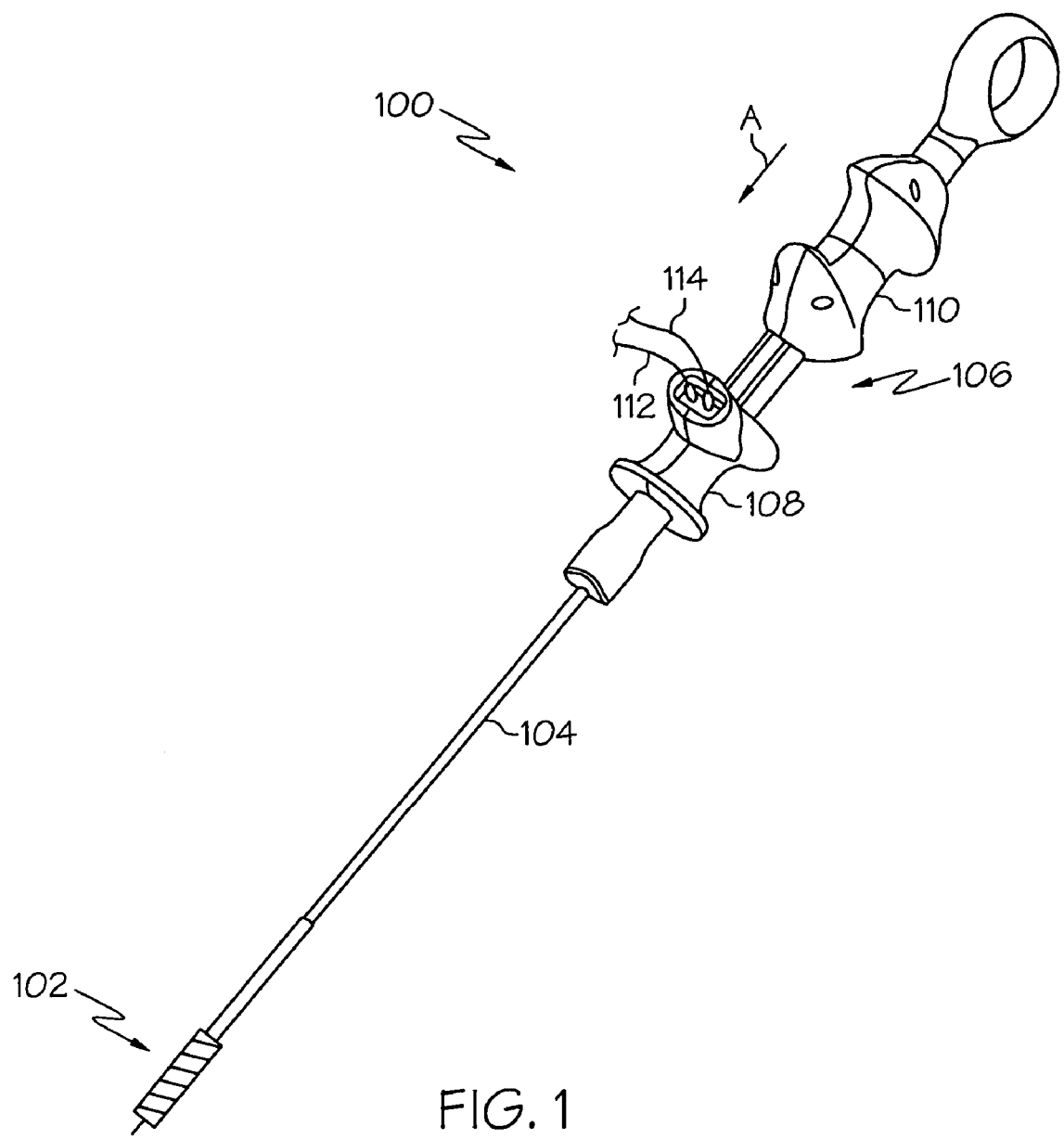
FIG. 1 is a perspective view of one aspect of the disclosed bipolar device.
Figure 5:
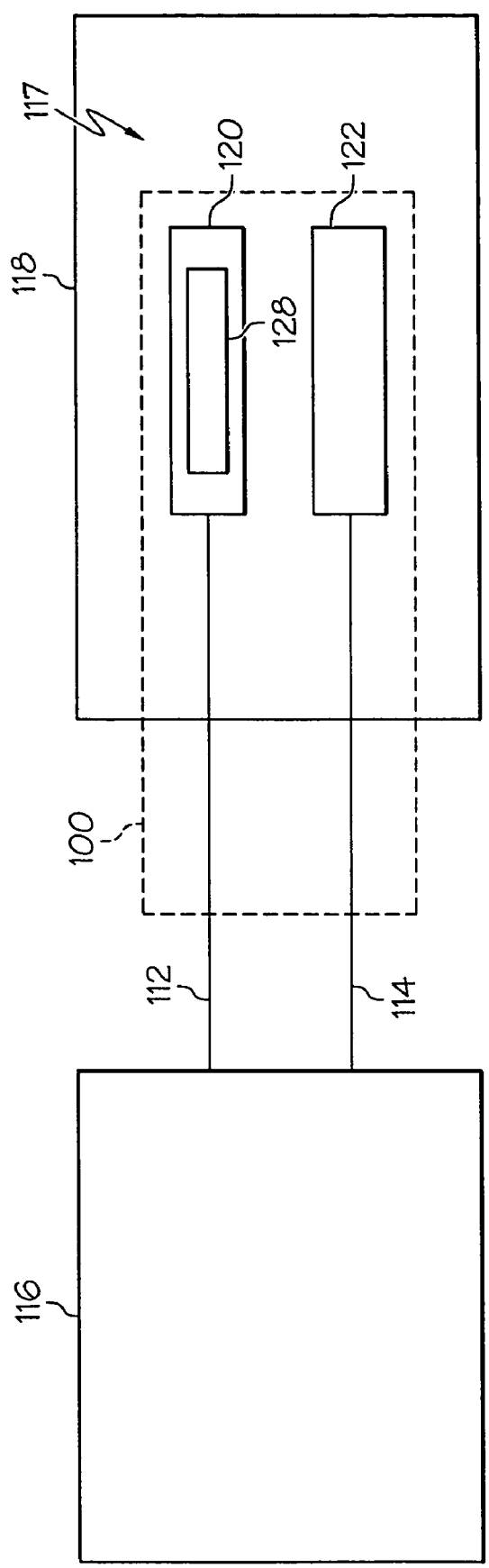
FIG. 5 is a block diagram of one aspect of a surgical system including the bipolar device of FIG. 1.

Referring to FIG. 1, one aspect of the disclosed bipolar device, generally designated 100, may include a working end 102, an elongated shaft 104, a handle assembly 106, which may include a base portion 108 and an actuator 110, such as a plunger or trigger, and two electrode wires 112, 114 extending from the base portion 108 for connecting the device 100 to a bipolar generator or other source of bipolar electrical energy 116 (FIG. 5). The shaft 104 may be flexible and may mechanically connect the working end 102 to the handle assembly 106. The entire device 100 may be sized and shaped to pass through a working channel 117 of an endoscope 118 (FIG. 5).

Figure 2:
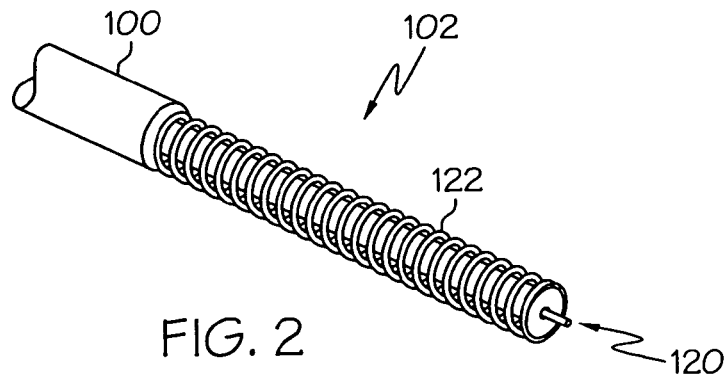
FIG. 2 is a perspective view of the working end of the device of FIG. 1.
Figure 3:
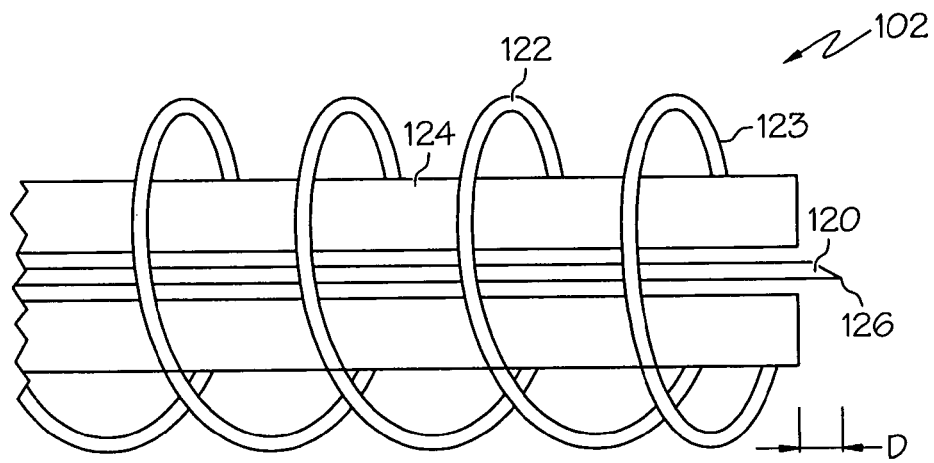
FIG. 3 is a side elevational view, partially in section, of the device of FIG. 2.
Figure 4:
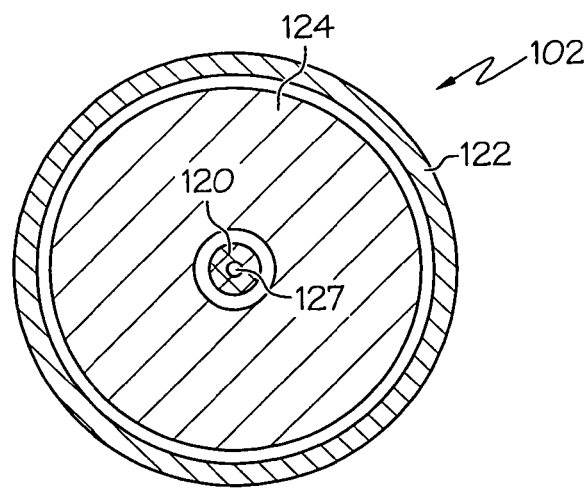
FIG. 4 is a front elevational view of the device of FIG. 2.

Referring to FIGS. 2-4, the working end 102 of the device 100 may include an injection needle 120 and a coaxial conductor 122. The coaxial conductor 122 may be electrically isolated from and coaxially disposed over the needle 120. In one aspect, the needle 120 may extend distally a predetermined distance D beyond the distal most end 123 of the conductor 122. Optionally, an insulator 124 may be disposed in the annular region between the needle 120 and the conductor 122 to facilitate electrical isolation of the needle 120 from the conductor 122.

In one aspect, the needle 120 may be a syringe-type needle and may include a penetrating tip 126 (FIG. 3) and an internal passageway 127 (FIG. 4). For example, the needle 120 may be a 25 gauge syringe needle having a 0.5 mm outer diameter. In one aspect, the needle 120 may be formed from an electrically conductive material, such as surgical grade stainless steel, and may be electrically connected to the bipolar generator 116 by way of the electrode wire 112 such that the needle 120 may function as a first electrode of the bipolar device 100.

In one aspect, the needle 120 may be coupled to the plunger portion 110 of the handle 106 such that, when the plunger portion 110 is urged in the direction shown by arrow A, an injectable agent 128 disposed within the internal passageway 127 of the needle 120 may be ejected from the needle 120 through the tip 126. Therefore, in one aspect, the needle 120 may function as a syringe.

The injectable agent 128 may be a sclerosing agent, such as alcohol, epinephrin or the like. However, those skilled in the art will appreciate that the needle 120 may be used to inject various substances and materials, such as analgesics, antibiotics, tissue markers or the like.

As shown in FIGS. 2 and 3, in one aspect, the coaxial conductor 122 may be shaped as a coil spring to allow the working end 102 of the device to flex as is passes through the working channel 117 of an endoscope 118. In another aspect, the coil spring shape of the conductor 122 may facilitate articulation of the working end 102 of the device 100 in response to user commands and/or inputs. Alternatively, the conductor 122 may be a continuous structure, such as a continuous cylindrical structure, disposed axially around the needle 120.

The conductor 122 may be formed from an electrically conductive material, such as surgical grade stainless steel, and may be electrically connected to the bipolar generator 116 (FIG. 5) by way of the electrode wire 114 such that the conductor 122 may function as a second electrode of the bipolar device 100.

The insulator 124 may be formed from any electrically insulating material, such as a biocompatible polymer material, a surgical rubber or the like. In one aspect, the insulator 124 may extend approximately the entire length of the needle 120 and/or the conductor 122. In another aspect, the insulator 124 may be disposed adjacent to the tip 126 of the needle 120.

Figure 6:
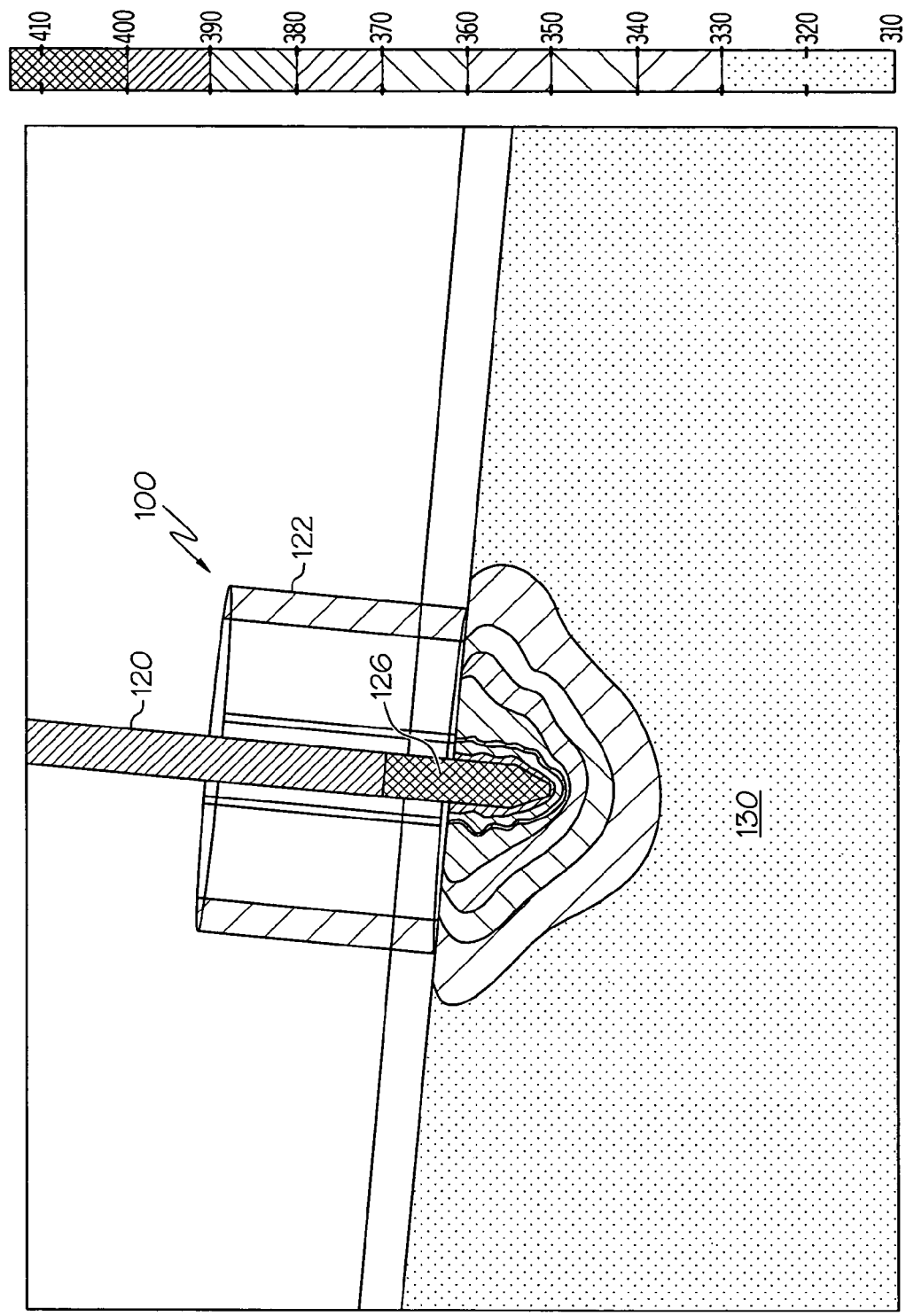
FIG. 6 is a graphical representation, based upon a finite element model, of the bipolar device of FIG. 1 treating tissue.

Reference will now be made to FIG. 6, which is a finite element model of one aspect of the bipolar device 100 described herein applying bipolar electrical energy to tissue 130. As shown in FIG. 6, the bipolar electrical energy may be directed below the surface of the tissue 130 and the heating that occurs as a result of the bipolar electrical energy may be confined to within the coaxial conductor 122.

Thus, the device 100 may be applied to tissue 130 (FIG. 6) such that the tip 126 of the needle 120 may penetrate the tissue 130 (e.g., the penetration may correspond to distance D of the tip 126) and the conductor 122 may abut the surface of the tissue 130. Therefore, when the bipolar energy is applied (e.g., about 20 to about 40 Watts for about 1 second), the energy may be confined to within the coaxial conductor 122 and may be applied below the surface of the tissue 130 (e.g., directly into a vessel), thereby limiting the amount of unnecessary tissue coagulation that occurs. Additionally, either simultaneously with or separately from the application of the electrical energy, the injectable agent 128 (e.g., a sclerosing agent) may be injected into the tissue 130.

Accordingly, the apparatus, systems and methods described herein allow a physician to apply electrical energy and an injectable agent to a target tissue area, while limiting the amount of damage that occurs to adjacent tissue, thereby reducing the risk of re-bleeding and shortening the required healing time.

Although various aspects of the disclosed bipolar apparatus, system and method have been shown and described, modifications may occur to those skilled in the art upon reading the specification. The present application includes such modifications and is limited only by the scope of the claims.

What is claimed is:

1. A surgical system comprising:
    a bipolar generator having a first electrical connection and a second electrical connection;
    a needle having a penetrating tip, said needle being formed from a first electrically conductive material and electrically connected to said first electrical connection;
    a coil spring coaxially disposed over and parallel with said needle to define an annular space therebetween, said coil spring being formed from a second electrically conductive material and electrically connected to said second electrical connection, wherein said penetrating tip extends distally beyond a distal end of said coil spring; and
    an electrical insulator disposed in said annular space, said electrical insulator terminating at a distal end, wherein said distal end of said coil spring is flush with said distal end of said electrical insulator.

2. The system of claim 1 wherein said needle includes an internal passageway.

3. The system of claim 2 further comprising an injectable agent disposed within said internal passageway.

4. The system of claim 3 wherein said injectable agent is a sclerosing agent.

5. The system of claim 1 wherein said needle is formed from a surgical grade stainless steel.

6. The system of claim 1 wherein said needle is a syringe needle of about 15 to about 35 gauge.

7. The system of claim 1 wherein said first electrically conductive material and said second electrically conductive material are the same.

8. The system of claim 1 wherein said coil spring is formed from a surgical grade stainless steel.

9. The system of claim 1 further comprising an elongated shaft having a proximal end and a distal end, wherein said needle and said coil spring are disposed at said distal end of said elongated shaft.

10. The system of claim 9 wherein said shaft, said needle and said coil spring are adapt to pass through a working channel of an endoscope.

11. The system of claim 9 further comprising a handle portion disposed at said proximal end, said handle portion including a actuator adapted to eject an injectable agent from said needle.

12. A method for treating a target tissue with a bipolar device including a needle and a coil spring, said method comprising the steps of:
    positioning said coil spring coaxially around said needle such that said needle is electrically isolated from said coil spring, wherein a penetrating tip portion of said needle extends distally beyond said coil spring;
    inserting said penetrating tip portion, but not said coil spring, into said target tissue; and
    electrically connecting said needle and said coil spring to a source of bipolar electrical energy such that electrical energy flows through said needle and said coil spring.

13. The method of claim 12 wherein said needle includes an internal passageway having an injectable agent disposed therein.

14. The method of claim 13 further comprising ejecting said injectable agent from said internal passageway and into said target tissue.

15. The method of claim 14 wherein said ejecting step and said electrically connecting step are performed simultaneously.

* * * * *